United States Patent
Stevens et al.

(10) Patent No.: US 10,675,247 B2
(45) Date of Patent: Jun. 9, 2020

(54) PRESS COATED TABLET PREPARED FOR DELAYED RELEASE OF AN ACTIVE INGREDIENT

(71) Applicant: Drug Delivery International Ltd., Glasgow, Strathclyde (GB)

(72) Inventors: Howard Norman Ernest Stevens, Strathclyde (GB); Alexander Balfour Mullen, Strathclyde (GB); David Smith, Strathclyde (GB); Fiona Jane Macdougall, Strathclyde (GB); Vivekanand Bhardwaj, Zionsville, IN (US)

(73) Assignee: Drug Delivery International Ltd., Glasgow, Strathclyde (GB)

( * ) Notice: Subject to any disclaimer, the term of this patent is extended or adjusted under 35 U.S.C. 154(b) by 0 days.

(21) Appl. No.: 15/526,655

(22) PCT Filed: Nov. 16, 2015

(86) PCT No.: PCT/GB2015/053471
§ 371 (c)(1),
(2) Date: May 12, 2017

(87) PCT Pub. No.: WO2015/075495
PCT Pub. Date: May 19, 2016

(65) Prior Publication Data
US 2017/0333355 A1    Nov. 23, 2017

(30) Foreign Application Priority Data
Nov. 14, 2014  (GB) .................................. 1420306.1

(51) Int. Cl.
*A61K 9/28*     (2006.01)
*A61K 31/00*    (2006.01)
*A61K 31/196*   (2006.01)

(52) U.S. Cl.
CPC ............. *A61K 9/2866* (2013.01); *A61K 9/282* (2013.01); *A61K 9/288* (2013.01); *A61K 31/00* (2013.01); *A61K 31/196* (2013.01)

(58) Field of Classification Search
None
See application file for complete search history.

(56) References Cited

U.S. PATENT DOCUMENTS

| | | | |
|---|---|---|---|
| 4,132,753 A | 1/1979 | Blichare et al. | |
| 5,126,145 A | 6/1992 | Evenstad et al. | |
| (Continued) | | | |

FOREIGN PATENT DOCUMENTS

| | | |
|---|---|---|
| CN | 1402631 | 3/2003 |
| CN | 103690545 A | 4/2014 |
| (Continued) | | |

OTHER PUBLICATIONS

Shin-Etsu product specification for Low-Substituted Hydroxypropyl Cellulose NF, Functional Disintegrant, available online Jun. 26, 2011 (Year: 2011).*

(Continued)

*Primary Examiner* — Robert A Wax
*Assistant Examiner* — Melissa S Mercier
(74) *Attorney, Agent, or Firm* — Suzannah K. Sundby, Esq.; Canady + Lortz LLP

(57) ABSTRACT

A press coated tablet for delayed release of an active ingredient comprising: (a) a core comprising one or more active ingredients, and; (b) an erodible delayed release barrier surrounding the core and comprising a wax and two or more grades of L-HPC, wherein the wax and L-HPC are provided in a weight ratio of wax to L-HPC of from 30%:70% to 70%:30%. The invention also relates to a method of making the press coated tablet.

24 Claims, 7 Drawing Sheets

(56) References Cited

U.S. PATENT DOCUMENTS

| | | | |
|---|---|---|---|
| 5,310,558 | A | 5/1994 | Pozzi et al. |
| 5,451,409 | A * | 9/1995 | Rencher ............... A61K 9/2054 424/468 |
| 5,690,959 | A | 11/1997 | Palepu et al. |
| 6,228,398 | B1 | 5/2001 | Devane et al. |
| 6,328,994 | B1 | 12/2001 | Shimizu et al. |
| 6,586,005 | B1 | 7/2003 | Raghuvanshi et al. |
| 6,869,963 | B2 * | 3/2005 | Patel ............... A61K 9/2009 514/307 |
| 7,220,430 | B2 | 5/2007 | Ishibashi et al. |
| 7,943,174 | B2 | 5/2011 | Oshlack et al. |
| 2002/0071870 | A1 | 6/2002 | Sharma |
| 2007/0129402 | A1 | 6/2007 | Ueki et al. |
| 2012/0177739 | A1 | 7/2012 | Vergnault et al. |
| 2017/0258731 | A1 | 9/2017 | Stevens et al. |

FOREIGN PATENT DOCUMENTS

| | | | |
|---|---|---|---|
| EP | 0074584 | A2 | 3/1983 |
| EP | 0097523 | A2 | 1/1984 |
| EP | 0277741 | A2 | 8/1988 |
| EP | 0418596 | A2 | 3/1991 |
| EP | 0671167 | A1 | 9/1995 |
| ES | 2274625 | T3 | 5/2007 |
| JP | 2003-095948 | A | 4/2003 |
| RU | 2236847 | C2 | 9/2004 |
| WO | 9319741 | A1 | 10/1993 |
| WO | 9427557 | A1 | 12/1994 |
| WO | 9959544 | A2 | 11/1999 |
| WO | 0074656 | A1 | 12/2000 |
| WO | 2001019349 | A1 | 3/2001 |
| WO | 2001032148 | A1 | 5/2001 |
| WO | 2004108082 | A2 | 12/2004 |
| WO | 2005041935 | A1 | 5/2005 |
| WO | 2005065673 | A1 | 7/2005 |
| WO | 2006017159 | A1 | 2/2006 |
| WO | 2006035313 | A1 | 4/2006 |
| WO | 2007052299 | A2 | 5/2007 |
| WO | 2008050987 | A1 | 5/2008 |
| WO | 2008157103 | A2 | 12/2008 |
| WO | 2009054550 | A1 | 4/2009 |
| WO | 2011107749 | A2 | 9/2011 |
| WO | 2011107750 | A2 | 9/2011 |
| WO | 2011107755 | A2 | 9/2011 |
| WO | WO-2011107749 | A2 * | 9/2011 ............. A61K 9/282 |
| WO | 2016075496 | A1 | 5/2016 |
| WO | 2016075497 | A1 | 5/2016 |

OTHER PUBLICATIONS

Shin-Etsu product specification for Low-Substituted Hydroxypropyl Cellulose NF, Functional Disintegrant, available online Jun. 26, 2011 (Year: 2011).*

Carter, "The role of disintegrants in solid oral dosage manufacturing", http://www.carterpharmaceuticalconsulting.com/articles/The-role-of-disintegrants.html. 3 pages.

Guo, et al., "Ion-exchange resins as drug delivery carriers", Journal of Pharmaceutical Sciences, Nov. 2009, vol. 98 (11):3886-3902.

Ghimire, et al., "In-vitro/in-vivo correlation of pulsatile drug release from press-coated tablet formulations: A pharmacoscintigraphic study in the beagle dog", European Journal of Pharmaceutics and Biopharmaceutics, 2007, 67: 512-523.

Stevens, "Chronopharmaceutical drug delivery", J. Pharm. Pharmacol., 1998, 50(s) 5.

Kawishima, et al., "Low-Substituted Hydroxypropylcellulose as a Sustained-Drug Release Matrix Base or Disintegrant Depending on Its Particle Size and Loading in Formulation", Pharmaceutical Research, 1993, 10 (3): 351-355.

Brief Chemical Encyclopedia, vol. 1, Moscow, 1961, p. 661.

Office Action received in CN106999438 dated Nov. 4, 2019.

Conte, et al., "Press-coated tablets for time-programmed release of drugs", Oct. 1993, pp. 1017-1023, vol. 14, No. 13, Publisher: Biomaterials (abstract).

Fukui, et al., "Studies on applicability of press-coated tablets using hydroxypropylcellulose (HPC) in the outer shell for timed-release preparations", Aug. 10, 2000, pp. 215-223, vol. 68, No. 2.

International Search Report received in PCT/GB2015/053471 dated Jan. 7, 2016.

Written Opinion received in PCT/GB2015/053471 dated Jan. 7, 2016.

Office Action received in RU7884426 dated Jun. 13, 2019.

* cited by examiner

PRESS COATED TABLET PREPARED FOR DELAYED RELEASE OF AN ACTIVE INGREDIENT

The present invention relates to a press coated tablet that provides a delayed release of active ingredient from the core of the tablet via erosion of a release barrier surrounding the core.

The ability to release active pharmaceutical ingredients after a delayed period is desirable for the treatment of many disease states. For example, those diseases that are affected by the circadian rhythm (see Stevens HNE Chronopharmaceutical Drug Delivery J. Pharm Pharmac., 50 (s) 5 (1998)). Treatments by orally administering an agent where it is desirable that the agent is released after a delayed period are known. Such treatments can be used to release drug while a subject is sleeping or to treat conditions according to a particular regimen. Such known time delayed release mechanisms utilise complex manufacturing processes and/or rely on a 'rupture' mechanism where contact with gastrointestinal fluids causes swelling of the tablet form and a structural burst that releases the drug after a defined period of time. Such a rupture mechanism may be characterised by the outer release barrier that surrounds a drug filled core rupturing abruptly following swelling of the tablet core, so as to form an opened 'clam-shell' configuration. Drug release via such mechanisms may be physically impeded in areas of the GI tract with poor motility, viscous or solid luminal contents, or faecal compaction, with limited water availability. Consequently, such known delayed release tablets may fail by never or incompletely opening and passing through the GI tract relatively intact without complete release of the drug, or result in release that is triggered after the tablet has passed the portion of the GI tract intended for local delivery of the drug.

Many strategies are available to the skilled person when designing a release barrier so as to control release of a drug from a core. Polymer membrane based constructions may be employed, but these tend to be complex and expensive and commonly utilise solvents for processing. An alternative and simpler strategy involves the construction of a release barrier that includes a wax and a disintegrant; the disintegrant swelling on exposure to liquid and causing a surface weakening in the release barrier that is substantially held together by the wax, to the point that the barrier starts to erode at the tablet surface, and gradually continues until all of the barrier layer is removed with subsequent release of the drug from the internal core tablet. The choice of disintegrants is however very wide and it is difficult to predict how they are going to interact in the GI tract when incorporated in a wax barrier.

One of the many optional disintegrants available is low-substituted hydroxypropyl cellulose (L-HPC). As L-HPCs are used in drug formulations, they are familiar to the skilled person. L-HPC is not soluble in water and instead absorbs water, thereby expanding in volume. As a result L-HPC is generally considered to be useful as a disintegrant by rapidly expanding in volume when in the presence of water, and is also available in grades which function as a binder. The advantages identified by the present inventors and derived from combining grades of L-HPC are however new. The IUPAC name for L-HPC is cellulose, 2, hydroxypropyl ether (low substituted). L-HPCs share the same CAS number with hydroxypropyl cellulose (i.e. 9004-64-2). L-HPC however differs from hydroxypropyl cellulose by the fact that it includes less hydroxypropoxy groups in the cellulose backbone. When dried at 105° C. for 1 hour, L-HPC contains not less than 5.0% and not more than 16.0% by weight of the molecule of hydroxypropoxy groups.

It has surprisingly been found that using combinations of L-HPC in a wax based release barrier offer an increased range of control of the release delay period, while maintaining the behavioural property of erosion. Typically, delayed release of the active agent in this invention is achieved by providing a press coated tablet comprising a delayed release layer surrounding a core comprising the active agent. The delayed release layer may comprise a wax and a combination of two or more different low substituted hydroxypropyl celluloses (L-HPC) grades, for example a combination of smaller (for example LH32) and larger particle sizes (for example LH21).

Accordingly, in the first aspect of the present invention, there is provided a press coated tablet for delayed release of an active ingredient, comprising:
(a) a core comprising one or more active ingredients, and;
(b) an erodible delayed release barrier surrounding the core and comprising a wax and two or more grades of L-HPC, wherein the wax and L-HPC are provided in a weight ratio of wax to L-HPC of from 30%:70% to 70%:30%.

The erodible delayed release barrier provides a delay of active ingredient release from the tablet. The nature and rate of release once initiated is dependent on the formulation of the core. Such core formulations may be able to release the active ingredient from the core in a sustained manner over a period of several hours after initiation of drug release, for example of between 2-12 hours. Alternatively, the core releases at least 70% of the active agent within 5-80 minutes after initiation of release. The erodible barrier layer functions independently of the formulation or active ingredient content of the core.

Not wishing to be restricted further, but in the interests of clarity, it is proposed that the formulations of the present invention are able to provide a delayed release profile, where the range of the delay period is more widely controllable than conventional wax and single L-HPC combinations, while maintaining a controlled erosion behaviour, as opposed to the rupture to an open clam shell mechanism of the prior art. Wax-containing delayed release mechanisms known in the art typically work through a swelling and rupture mechanism rather than the erosion mechanism of the present invention (see US2012/0177739A1 Vergnault et al.) The present method uses the combination of L-HPC grades to provide a prolonged delay period while retaining the erosion of the barrier layer.

It is surprising that an erosion mechanism is able to provide such wide ranging control of the delay time, as the few known erosion-based controlled delayed release technologies are unable to provide such extended lag periods before drug release in combination with an erosion process. See, for example, Ghimire et al. *European Journal Pharmaceutics* (67) 2007 515-523. The erosion mechanism ensures steady and reproducible release in vitro and in vivo, independent of location of the tablet in the GI tract. The use of an erosion mechanism to achieve the delayed release overcomes potential difficulties faced by other delayed release technologies known in the art that use a swell and rupture system. Further, this technology uses a more simple manufacturing process than other technologies known in the art. Such formulations could be used for, but are not limited to, providing night-time dosing, for example in the treatment of insomnia; for treatment of early morning conditions such as morning stiffness associated with arthritic conditions or reduction of periods of increased cardiovascular risks such as myocardial infarction; or for other timed dosing regimens.

L-HPCs may be graded; for example by particle size or by hydroxypropoxy content.

When L-HPCs are graded by particle size, they are normally graded into coarse particles, medium sized particles or micronized particles.

Coarse particles may have a mean particle size of 50 µm and above, from 50 µm to 65 µm or from 53 µm to 57 µm. Coarse particles may have a mean particle size 55 µm. An example of a coarse particle L-HPC may be LH-11 and/or LH-B1.

Medium sized particles may have a mean particle size of less than 50 µm to 30 µm, less than 50 µm to 40 µm or from 42 µm to 48 µm. Medium sized particles may have a mean particle size of 45 µm. Examples of medium sized L-HPCs may be any one or more of LH-21, LH-22, NBD-22, NBD-021 and/or NBD-020.

Micronised particles may have a mean particle size of less than 30 µm, less than 30 µm to 1 µm, less than 30 µm to 10 µm, from 15 µm to 25 µm or from 17 µm to 23 µm. Micronised particles may have a mean particle size of 20 µm. Examples of micronised L-HPCs are LH-31 and/or LH-32.

The skilled person would be well aware of appropriate ways in order to determine mean particle size. Merely as an example, mean particle size may be established in accordance with Sympatec's protocols for use of their laser diffraction system (eg HELOS or MYTOS).

When L-HPCs are graded by hydroxypropoxy content, they are normally graded into high or low level hydroxypropoxy content (high and low being relative terms applying to L-HPCs).

L-HPCs with high level hydroxypropoxy content may have a content of 10% or greater, from 10% to 16%, from 10% to 15%, from 10% to 14%, from 10% to 13% or from 10% to 12%. L-HPCs with high level hydroxypropoxy content may have a content of 11%. Examples of L-HPCs with high level hydroxypropoxy content may be any one or more of NBD-021, NBD-020, LH-11, LH-21, LH-31 and/or LH-B1.

L-HPCs with low level hydroxypropoxy content may have a content of less than 10%, less than 10% to 5%, less than 10% to 6%, from 5% to 9%, from 6% to 9%, from 7% to 9% or from 8% to 9%. L-HPCs with low level hydroxypropoxy content may have a content of 8%. Examples of L-HPCs with low level hydroxypropoxy content may be any one or more of NBD-022, LH-22 and/or LH-32.

A press coated tablet according to the present invention may, for example, include any one or combination of the L-HPC's chosen from the list of LH-11, LH-21, LH-22, LH-32, LH-B1, LH-31, NBD-22, NBD-021 and NBD-020.

As the release barrier includes two or more grades of L-HPC, the release barrier can be seen to include a blend of L-HPC grades.

For example, the release barrier could include at least two grades of L-HPC selected from the group consisting of coarse particle L-HPC, medium particle L-HPC and micronised particle L-HPC. Alternatively, or additionally, the release barrier could include a low and a high level hydroxypropoxy content L-HPC. For example, the release barrier could include:

a) coarse and medium particle L-HPCs (e.g. any one of the following combinations: LH-11 and LH-21, LH-11 and LH-22, LH-11 and NBD-22, LH-11 and NBD-021, LH-11 and NBD-020, LH-B1 and LH-21, LH-B1 and LH-22, LH-B1 and NBD-22, LH-B1 and NBD-021, LH-B1 and NBD-020);

b) coarse and micronised particle L-HPCs (e.g. any one of the following combinations: LH-11 and LH-31, LH-11 and LH-32, LH-B1 and LH-31, and LH-B1 and LH-32);

c) medium and micronised particle L-HPCs (e.g. any one of the following combinations: LH-21 and LH-31, LH-22 and LH-31, NBD-22 and LH-31, NBD-021 and LH-31, NBD-020 and LH-31, LH-21 and LH-32, LH-22 and LH-32, NBD-22 and LH-32, NBD-021 and LH-32, and NBD-020 and LH-32);

d) a low and a high level hydroxypropoxy content L-HPCs (e.g. any one of the following combinations: NBD-021 and NBD-022, NBD-020 and NBD-022, LH-11 and NBD-022, LH-21 and NBD-022, LH-31 and NBD-022, LH-B1 and NBD-022, NBD-021 and LH-22, NBD-020 and LH-22, LH-11 and LH-22, LH-21 and LH-22, LH-31 and LH-22, LH-B1 and LH-22, NBD-021 and LH-32, NBD-020 and LH-32, LH-11 and LH-32, LH-21 and LH-32, LH-31 and LH-32, and LH-B1 and LH-32);

e) a low and a high level hydroxypropoxy content L-HPCs that are also a combination of coarse and medium particle L-HPC (e.g. any one of the following combinations: LH-11 and LH-22, LH11 and NBD-022, LH-B1 and LH-22, and LH-B1 and NBD-022);

f) a low and a high level hydroxypropoxy content L-HPCs that are also a combination of coarse and micronised particle L-HPC (e.g. any one of the following combinations: LH-11 and LH-32, and LH-B1 and LH-32), or;

g) a low and a high level hydroxypropoxy content L-HPCs that are also a combination of medium and micronised particle L-HPC (e.g. any one of the following combinations: LH-22 and LH-31, NBD-022 and LH-31, LH-21 and LH-32, NBD-021 and LH-32, and NBD-020 and LH 32).

Consequently, for example, the press coated tablet of the present invention may comprise:

(a) a core comprising one or more active ingredients, and;
(b) an erodible delayed release barrier surrounding the core and comprising a wax, LH-21 and LH-32, wherein the wax and total L-HPC are provided in a weight ratio of wax to total L-HPC of from 30%:70% to 70%:30%.

Alternative combinations may be selected, for example, combinations that include NBD-022 and LH-32.

The weight ratio of one L-HPC grade to the other L-HPC grade in the release barrier may be from 5%:95% to 95%:5%, from 15%:85% to 85%:15%, or from 30%:70% to 70%:30%. The ratio of each grade of L-HPC may be controlled to achieve the ideal release profile.

Providing an increased amount of a coarse and/or high level hydroxypropoxy content L-HPC relative to a medium, micronised and/or low level hydroxypropoxy content L-HPC in the release barrier may increase the rate of erosion.

For example using a weight ratio of coarse and/or high level hydroxypropoxy content L-HPC: medium, micronised and/or low level hydroxypropoxy content L-HPC of >50%:<50%, >55%:<45%, >60%:<40%, >70%:<30%, >80%:<20% or >90%:<10%. Consequently, the release barrier may include more LH-11 than LH-32. The wax of the present invention may be any pharmaceutically acceptable wax capable of binding together the contents of the release layer to the outside of the core. The skilled person would be well aware of suitable waxes, for example, the wax may be chosen from any of the group consisting of beeswax, microcrystalline wax, a glyceryl ester, hydrogenated castor oil or carnauba wax or any combinations of waxes. The wax may be glycerol behenate. The wax and L-HPC may be provided in a ratio of 30:70 to 70:30% by weight, 30:70 to 65:35% by weight, 30:70 to 60:40% by weight, 30:70 to 55:45% by weight, or 30:70 to 50:50% by weight.

The delayed release barrier according to the present invention is erodible. This is a term of art that would be familiar to the skilled person. However, for the avoidance of doubt, the term may be understood to mean that the delayed release barrier layer is continuously liberated from the tablet. This process is gradual, taking from 2 to 12 hours. This process can function adequately even in the presence of relatively small amounts of water.

The core comprises one or more active ingredient. The core may also comprise any other pharmaceutically acceptable excipients or diluents. The core may include a matrix in which the one or more active ingredient is provided. Matrices suitable for retaining and releasing active ingredients in a sustained manner are well known to the skilled person.

The active ingredient may be any agent used in methods of therapeutic (including prophylactic) treatment. It has been demonstrated that a tablet formulated according to the present invention may be a vehicle for the administration of any therapeutic agent. For example, the active ingredient may be any agent for use in the treatment of any one or more of the following: Central nervous system disorders (e.g. neurogenic pain, stroke, dementia, alzheimer's disease, parkinson's disease, neuronal degeneration, meningitis, spinal cord injury, cerebral vasospasm, amyotrophic lateral sclerosis), cardiovascular disease (e.g. hypertension, atherosclerosis, angina, arterial obstruction, peripheral arterial disease, myocardial pathology, arrhythmia, acute myocardial infarction, cardiomyopathy, congestive heart failure, coronary artery disease (CAD), carotid artery disease, endocarditis, hypercholesterolemia, hyperlipidemia, peripheral artery disease (PAD), or any combination thereof), Genitourinary disorders (e.g. erectile dysfunction, urinary organ diseases benign prostatic hypertrophy (BPH), renal tubular acidosis, diabetic nephropathy, glomerulonephritis, glomerulosclerosis, urinary tract infection, faecal incontinence, or any combination thereof), ocular disease (e.g. glaucoma, blepharitis, ocular hypertension, retinopathy, conjunctivitis, scleritis, retinitis, keratitis, corneal ulcer, iritis, chorioretinal inflammation, macular edema, xerophthalmia, or any combination thereof), pulmonary disease (e.g. asthma, pulmonary hypertension, acute respiratory distress syndrome, COPD, emphysema, pneumonia, tuberculosis, bronchitis, acute bronchitis, bronchiectasis, bronchiolitis, bronchopulmonary dysplasia, byssinosis, coccidioidomycosis (Cocci), cystic fibrosis, influenza, lung cancer, mesothelioma, or any combination thereof), metabolic diseases (e.g. hypercalciuria, hyperglycemia, hyperinsulinemic hypoglycemia, hyperinsulinism, hyperlysinuria, hypoglycemia or any combination thereof), Exocrine and endocrine diseases (e.g. addison's disease, hypoaldosteronism, cushing's syndrome, diabetes, goitre, hyperthyroidism, hypothyroidism, thyroiditis, pancreatitis or any combination thereof), Hepatic disorders (e.g. hepatitis, non-alcoholic fatty liver disease, cirrhosis, hepatic cancer, primary sclerosing cholangitis, primary biliary cirrhosis, budd-chiari syndrome or any combination thereof), Autoimmune and inflammatory diseases (e.g. multiple sclerosis rheumatoid arthritis, psoriasis, diabetes, sarcoidosis, addison's disease, alopecia areata, amyotrophic lateral sclerosis, ankylosing spondylitis, polyarticular arthritis, atopic allergy, topic dermatitis, autoimmune hepatitis, celiac disease, chagas disease, coeliac disease, cogan syndrome, crohns disease, cushing's syndrome, diabetes mellitus type 1, endometriosis, eosinophilic fasciitis, fibromyalgia/fibromyositis, gastritis, glomerulonephritis, graves' disease. guillain-barré syndrome (GBS), hashimoto's encephalitis, hashimoto's thyroiditis, haemolytic anaemia, idiopathic inflammatory demyelinating diseases, idiopathic pulmonary fibrosis, interstitial cystitis, juvenile idiopathic arthritis, juvenile rheumatoid arthritis, kawasaki's disease, lichen sclerosis, lupus erythematosus, ménière's disease, myasthenia gravis, myositis, narcolepsy, pernicious anaemia, perivenous encephalomyelitis, polymyalgia rheumatica, primary biliary cirrhosis, psoriatic arthritis, reiter's syndrome, rheumatoid fever, sarcoidosis, schizophrenia, sjögren's syndrome, spondyloarthropathy, ulcerative colitis or any combination thereof), Musculoskeletal disorders (e.g. osteoarthritis, osteoporosis, osteonecrosis, arthritis, paget's disease bursitis, costochondritis, tendonitis or any combination thereof), Skin disorders (e.g. acne, alopecia, candidiasis, celluliltis, dermatitis, eczema, epidermolysis bullosa, erythrasma, herpes, erysipelas, folliculitis, impetigo, ringworm, scabies, tinea, trichomycosis or any combination thereof), ENT disorders (e.g. otitis, sinusitis, laryngitis, pharyngitis, laryngitis, meniere's disease, labyrinthitis, or any combination thereof), gastro-intestinal disorders (e.g. irritable bowel syndrome (IBS) necrotizing entercolitis (NEC) non-ulcer dyspepsia, chronic intestinal pseudo-obstruction, functional dyspepsia, colonic pseudo-obstructioduodenogastric reflux, gastroesophageal reflux disease, ileus inflammation, gastroparesis, heartburn, constipation—for example constipation associated with use for medications such as opioids-, colorectal cancer, colonic polyps, diverticulitis, colorectal cancer, barretts esophagus, bleeding in the digestive tract, celiac disease, colon polyps, constipation, crohn's disease, cyclic vomiting syndrome, delayed gastric emptying (gastroparesis), diarrhea, diverticulosis, duodenal ulcers, fecal incontinence, gallstones, gas in the digestive tract, gastritis, gastroesophageal reflux disease (GERD), heartburn, hiatal hernia, hemochromatosis, hemorrhoids, hiatal hernia, hirschsprung's disease, indigestion, inguinal hernia, lactose intolerance, peptic ulcers, polyps, porphyria, primary biliary cirrhosis, primary sclerosing cholangitis, proctitis, rapid gastric emptying, short bowel syndrome, stomach ulcers, ulcerative colitis, ulcers, whipples disease, or any combination thereof), acute and/or chronic pain, viral infection, cancer, laryngitis, mastoiditis, myringitis, otitis media, rhinitis, sinusitis, sialadenitis, tonsillopharyngitis, or any combination thereof.

Consequently, the active ingredient may be any one or combination of paracetamol, metformin and diclofenac.

As mentioned above, the delayed release barrier surrounds the core. The release barrier may be provided in a thickness of from 0.5 mm to 3 mm+/−10% across the surface of the core. One or more functionalised layers may be provided between the core and the delayed release barrier.

The tablets of the present invention are press coated tablets. The skilled person would be well aware of this term of art. However, for the avoidance of doubt, press coated tablets are those with a core that is coated by a layer (e.g. delay barrier) that is applied by pressure to the external surface of the core.

The press coated tablet may include one or more coatings that can be pH dependent or independent or may be functional or aesthetic and may optionally contain an active ingredient. The one or more coating may be a gastro-resistant coating intended to prevent release in the stomach, with which the clock for delayed release does not therefore start until the tablet has passed through the stomach. Such one or more coatings can be external to the delayed release barrier.

The delayed release barrier and/or one or more coating/s may further comprise an active ingredient. The active ingredient in the delayed release barrier and/or one or more coating may be the same as or different to the active ingredient or ingredients of the core. Alternatively, the delayed release barrier and/or other coatings do not include active ingredient.

As is clear from above, control of release and lag time for release may be controlled by any one or combination of:
1) The ratio of L-HPC to wax;
2) The thickness of the barrier layer that is compressed onto the core tablet, and;
3) The ratio of different L-HPC grades with respect to each other.

The tablet may further comprise a top layer (i.e. external layer to the core and erodible delayed release layer, possibly the most outer layer) which may contain an optional immediate release layer comprising the same or different drug to that in the core. A coating as described above may be added to a tablet of this design, or alternatively the top layer may be added to an already coated tablet as described earlier.

In a second aspect of the present invention, there is provided a method of making a press coated tablet according to the first aspect of the present invention, the method comprising the steps of:
a) the active ingredient and pharmaceutically acceptable excipients and/or diluents are mixed and compressed to form a core;
b) one or more wax and two or more L-HPCs are mixed and the resulting mixture compressed around the outer surface of the core so as to form a barrier layer.

All features of the first aspect of the present invention may be understood to apply to the second aspect of the present invention.

The active ingredient may be granulated with pharmaceutically acceptable excipients and/or diluents, optionally in a wet granulation method, or blended as a dry powder mix prior to forming the compressed core. The granules or core powder blend may be mixed with additional pharmaceutically acceptable excipients and/or diluents prior to forming the compressed core. The core may be made by alternative means, for example by injection moulding or by 3D printing.

The wax may be heated prior to mixing with the L-HPCs so as to form granules on agitation or granulating with cooling, or may be mixed with the L-HPCs then heated together in a hot melt granulation process prior to being compressed around the outer surface of the core.

Unless indicated to the contrary, all conditions provided herein are measured at 100 kPa (ie 0.987 atm, 1 bar) and at 20° C.

Unless indicated to the contrary, where the invention is defined in terms of features selected from a list, or any combination thereof, each combination is contemplated as being disclosed individually herein as a single optional recited feature that may form part of the present invention.

All optional features of the present invention may be combined with other optional features of the present invention, unless context excludes this possibility.

The present invention will now be described, by way of example, with reference to the figures, in which:

FIG. 1 shows a diagram of the delayed release tablet of the present invention comprising a drug-containing core tablet that may be either immediate or sustained release and an outer erodible barrier layer that controls the delay of release.

Reference numeral 1 shows the tablet core while reference numeral 2 the erodible barrier layer.

FIG. 2 shows dissolution profiles obtained for tablets according to the present invention with different ratios of wax:disintegrant in the composition of the barrier layer, a fixed release barrier weight and a fixed LH21:32 ratio FIG. 3 shows dissolution profiles obtained for tablets according to the present invention with the wax content in the release barrier being kept constant, as has the ratio of the combined L-HPCs, but the combinations of L-HPCs varied.

1. TABLET STRUCTURE

Figure 1:
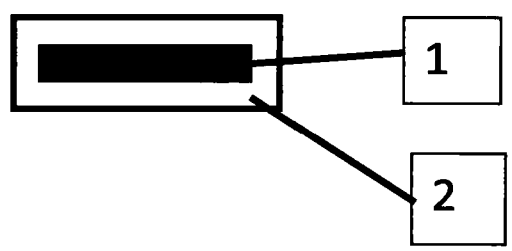

The formulation of the invention provides a treatment for the delayed release of an active ingredient or ingredients. The formulation is a press coated tablet manufactured by simple, well understood pharmaceutical processes. Control of the lag period prior to release is achieved by steady erosion of a barrier layer that is compression coated around a drug-containing core tablet to form a tablet in tablet structure (FIG. 1). Control of erosion over a prolonged period is achieved by combining two or more different grades of Low substituted hydroxypropyl celluloses (L-HPC) preferably with different particle sizes and preferably at least one small particle size and one large particle size.

2. MANUFACTURE OF CORE TABLET

Any core tablet may be used providing it is of an appropriate size for ingestion, e.g. by a human. In this example the following wet granulation process was used to provide an immediate release core tablet.

| API/Excipient | % (w/w) | Location |
|---|---|---|
| Diclofenac potassium | 25 | Intra-granular |
| Microcrystalline cellulose (Avicel PH 101) | 63 | |
| Croscarmellose sodium (AC-DI-SOL) | 1 | |
| Croscarmellose sodium (AC-DI-SOL) | 10 | Extra-granular |
| Magnesium stearate | 1 | |

Weight of water used in granulation process is approximately 72% w/w of final blend weight (or 81% w/w of intragranular blend weight). 100 mg of the core blend is pressed to a hardness of 4-5 kp and a thickness of 3.4 mm±0.17 mm using a 6 mm bi-convex punch and die.

3. MANUFACTURE OF ERODIBLE BARRIER LAYER GRANULES

| Excipient | % (w/w) |
|---|---|
| Glycerol behenate (GB) | 42 |
| Low-substituted hydroxypropyl cellulose (LH-32) | 36 |
| Low-substituted hydroxypropyl cellulose (LH-21) | 22 |

All excipients are blended using a tumbling action for 5 minutes.

The blend is processed by hot melt granulation (although other appropriate melt granulation process are suitable). While still warm, the granules are passed through an oscillating granulator with a 1 mm sieve and collected.

Formulation Compression:

Erodible barrier layer granules are compressed around the 6 mm core tablet using standard compression coating techniques using a 10 mm biconvex punch and die to a hardness of between 5 and 10 Kiloponds. The core tablet is completely coated with an even layer of the granules.

4. IN VITRO DRUG RELEASE STUDIES

Dissolution studies were carried out on tablets prepared according to the present invention using an automated ADT8 USP dissolution type II apparatus (TDTO8L Bath 1105230, Electrolab Inc., Cupertino, USA), with paddle operated at 50 rpm, at 37° C.±0.5° C. Dissolution was carried out in 900 ml of pH6.8 phosphate buffer. Samples of dissolution media were withdrawn every 5 minutes and measured by UV analysis using an SP700 High Performance UV Visibility Spectrometer (T70+18-1815-1-0054, PG Instruments Ltd., Wibtoft, U.K.). Appropriate standard samples for the active ingredient per tablet preparations were measured prior to dissolution, using pH 6.8 phosphate buffer as a blank, to provide absorbance for 100% drug release.

5. EFFECT OF CHANGE OF PROPORTION OF L-HPCS IN BLEND ON RELEASE

TABLE 1

| Excipient Ratio GB:LH-11:LH-32 | Lag time achieved 4 hr formulation | Lag time achieved 6 hr formulation | Erosion observed? |
|---|---|---|---|
| 42:14.5:43.5 | 4 hrs 6 min | 6 hrs 5 min | Negligible |
| 42:17.4:40.6 | 3 hrs 53 min | 5 hrs 13 min | Yes |
| 42:20.3:37.7 | 3 hrs 26 min | 4 hrs 55 min | Good |

Table 1 shows the results of an examination of the release profile (as described in 4. above) of diclofenac potassium from a composition according to the present invention and manufactured according to that described in numbered paragraphs 2 and 3 above, with proportions of wax to L-HPC as shown in table 1. The amount of glycerol behenate (i.e. wax) in each tested tablet was kept constant, whilst the proportion of L-HPC was varied. The results clearly show that mixing the proportion of one grade of L-HPC to another grade in the release barrier can control the erosion of the delayed release layer and subsequently the time of release from the core.

6. EFFECT OF INCREASED WEIGHT OF DELAYED RELEASE BARRIER ON RELEASE OF ACTIVE INGREDIENT

TABLE 2

| Thickness of erosion layer for GB:LH-21:LH-32 ratio of 42:20.3:37.7 | Time of release |
|---|---|
| 260 mg | 3 hrs 26 mins |
| 290 mg | 4 hrs 3 mins |
| 300 mg | 4 hrs 11 mins |
| 330 mg | 4 hrs 40 mins |

Table 2 shows the results of an examination of the release profile (as described in 4. above) of diclofenac potassium from a composition according to the present invention and manufactured according to that described in numbered paragraphs 2 and 3 above, with proportions of wax to L-HPC as shown in table 2. The results demonstrate that an increase in thickness of release barrier corresponds to an increase in the lag time for release of the diclofenac potassium; thereby demonstrating the controllability of release by control of the thickness of the release barrier of the present invention.

6. EFFECT OF VARIATION OF PROPORTION OF WAX TO L-HPC IN RELEASE BARRIER

An examination of the release profile (as described in 4. above) of diclofenac potassium from a composition according to the present invention and manufactured according to that described in numbered paragraphs 2 and 3 above, with proportions of wax to L-HPC as shown below. Ratios of wax to disintegrant were used from 30:70 to 70:30 (with fixed LH 21:32 ratio and constant release barrier weight):

i. 30:70 (maintain LH21:LH32 ratio of 38:68)

ii. 40:60 (maintain LH21:LH32 ratio of 38:68)

iii. 50:50 (maintain LH21:LH32 ratio of 38:68)

iv. 70:30 (maintain LH21:LH32 ratio of 38:68)

Figure 2:
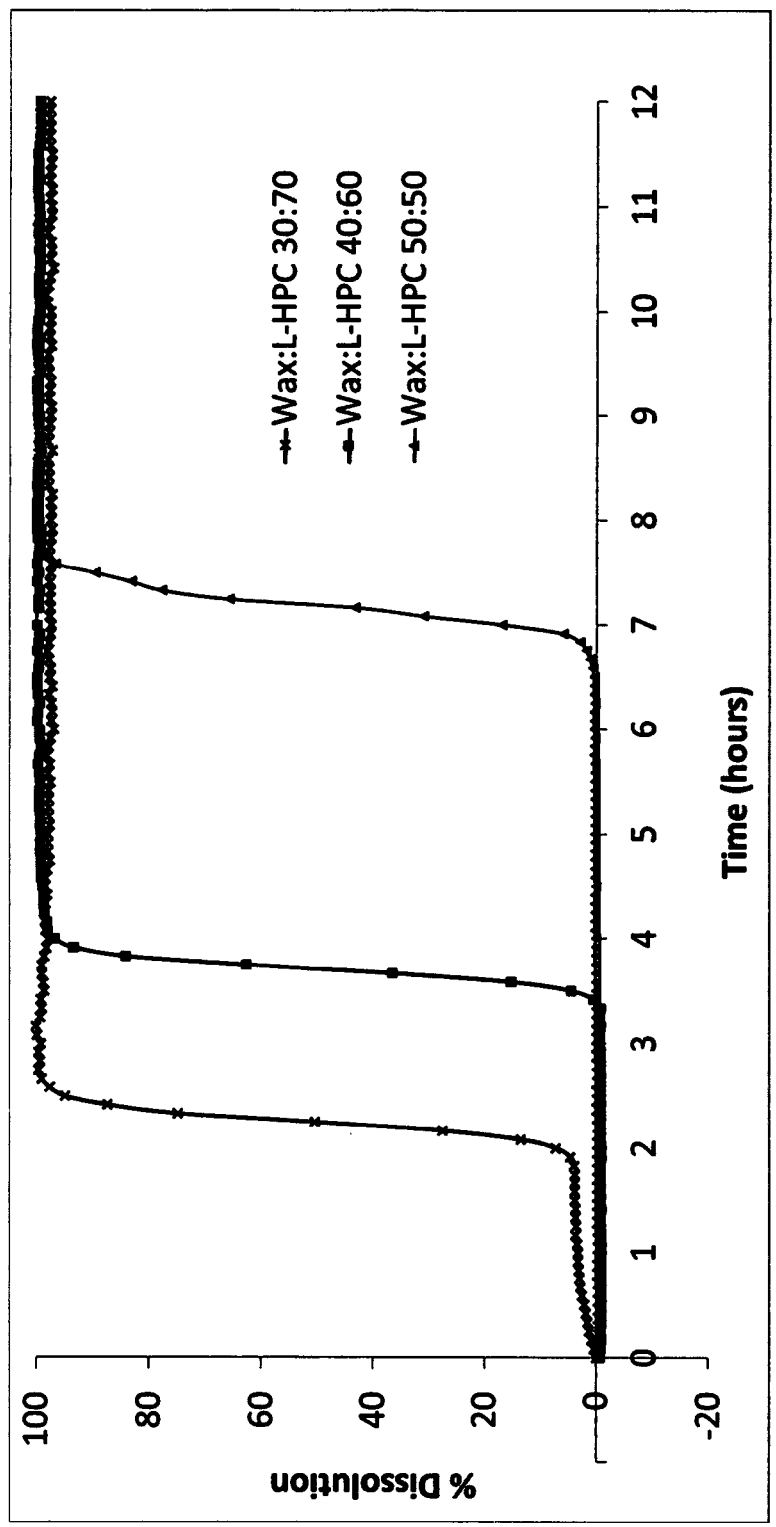

The results are shown in FIG. 2, and tables 3 and 4. As the wax content of the release barrier increases the lag time before release becomes longer. It was found here that with the LH mix composition used, the 70:30 tablet did not release the active from the core tablet during the time-frame of the study.

TABLE 3

| Wax:L-H PC | 30:70 | 40:60 | 50:50 | 70:30 |
|---|---|---|---|---|
| Average release time (hh:mm) | 02:02 | 03:30 | 06:57 | No Release |
| Standard deviation | 00:05 | 00:07 | 00:15 | No Release |
| RSD (%) | 4.3 | 3.4 | 3.8 | No Release |

Dissolution data obtained with different ratios of wax: disintegrant in the composition of the barrier layer, a fixed release barrier release barrier weight and a fixed LH21:32 ratio, showing the effect of total wax content on delay before—release, with diclofenac contained in the immediate release core.

TABLE 4

| Excipient | Wax:L-HPC | | | |
|---|---|---|---|---|
| | 30:70 % (w/w) | 40:60 % (w/w) | 50:50 % (w/w) | 70:30 % (w/w) |
| Glycerol behenate (GB) | 30 | 40 | 50 | 70 |
| Low-substituted hydroxypropyl cellulose (LH-32) | 43.4 | 37.25 | 31.15 | 11.35 |
| Low-substituted hydroxypropyl cellulose (LH-21) | 26.6 | 22.75 | 18.85 | 18.65 |

Composition of formulations used to obtain above dissolution profiles with different ratios of wax:disintegrant in the composition of the barrier layer, and a fixed LH21:32 ratio.

7. EFFECT OF GRADE COMBINATIONS OF L-HPC ON DISSOLUTION PROFILE

Figure 3:
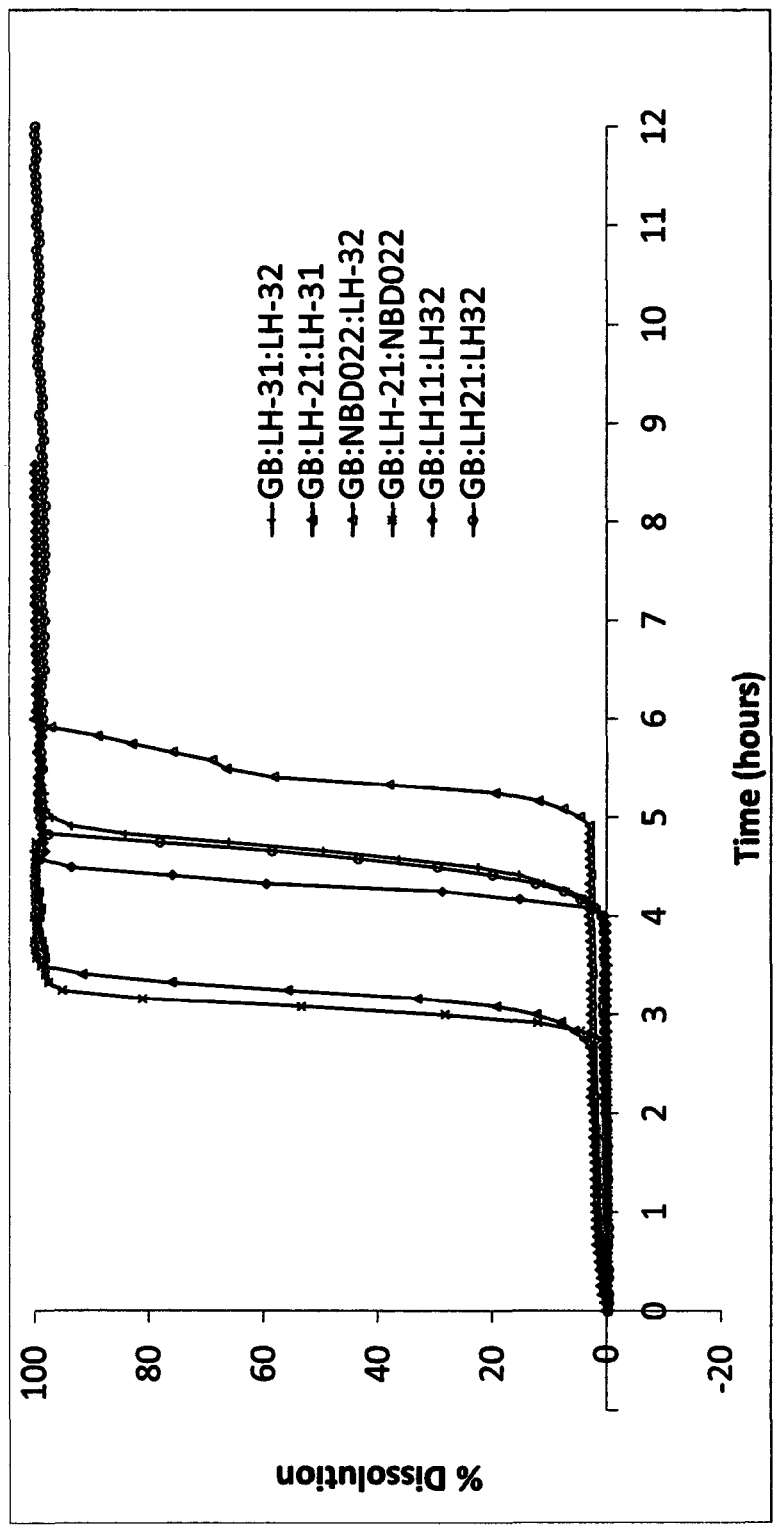

FIG. 3 shows the results of an examination of the release profile (as described in 4. above) of diclofenac potassium from a composition according to the present invention and manufactured according to that described in numbered paragraphs 2 and 3 above, with proportions of wax and combinations of L-HPC as shown in table 5. The wax content in the release barrier has been kept constant, as has the ratio of the combined L-HPCs.

The data below shows that combining grades of L-HPCs with different chemistry within the same fixed ratio in the barrier layer can have a significant effect on the lag time to release of active ingredient. Thereby demonstrating that good levels of control of the release profile may be achieved by control over the L-HPC combination.

TABLE 5

| Composition | GB: LH-31: LH-32 (42:22:36) | GB: LH-21: LH-31 (42:22:36) | GB: NBD022: LH-32 (42:22:36) | GB: LH-21: NBD022 (42:22:36) | GB:LH11: LH32 (42:14.5: 43.5) |
|---|---|---|---|---|---|
| Average release time (hh:mm) | 04:17 | 02:59 | 05:07 | 02:55 | 04:06 |
| Standard deviation | 00:13 | 00:10 | 00:19 | 00:08 | 00:11 |
| RSD (%) | 5.3177 | 5.9637 | 6.4837 | 5.1110 | 4.6812 |

Whilst it can be seen that generally selecting combinations of L-HPCs with high level hydroxypropoxy content provides a shorter delay period (see LH-21 and LH-31 combination), and selecting combinations of L-HPCs with low level hydroxypropyl content provides a longer delay period (see NBD-022 and LH-32), selecting L-HPCs with combinations of hydroxypropoxy content provide intermediate release lag times. Additionally, selecting combinations of L-HPCs with vastly different particles sizes can significantly change the release lag time; compare the results for LH-21 and NBD-022 (both with medium sized particles) with those of LH-11 and LH-32 (that provide course and micronised particles, respectively).

8. EFFECT OF PROPORTION OF L-HPC COMBINATION IN RELEASE BARRIER WITH CONSTANT WEIGHT AND WAX

Figure 4:
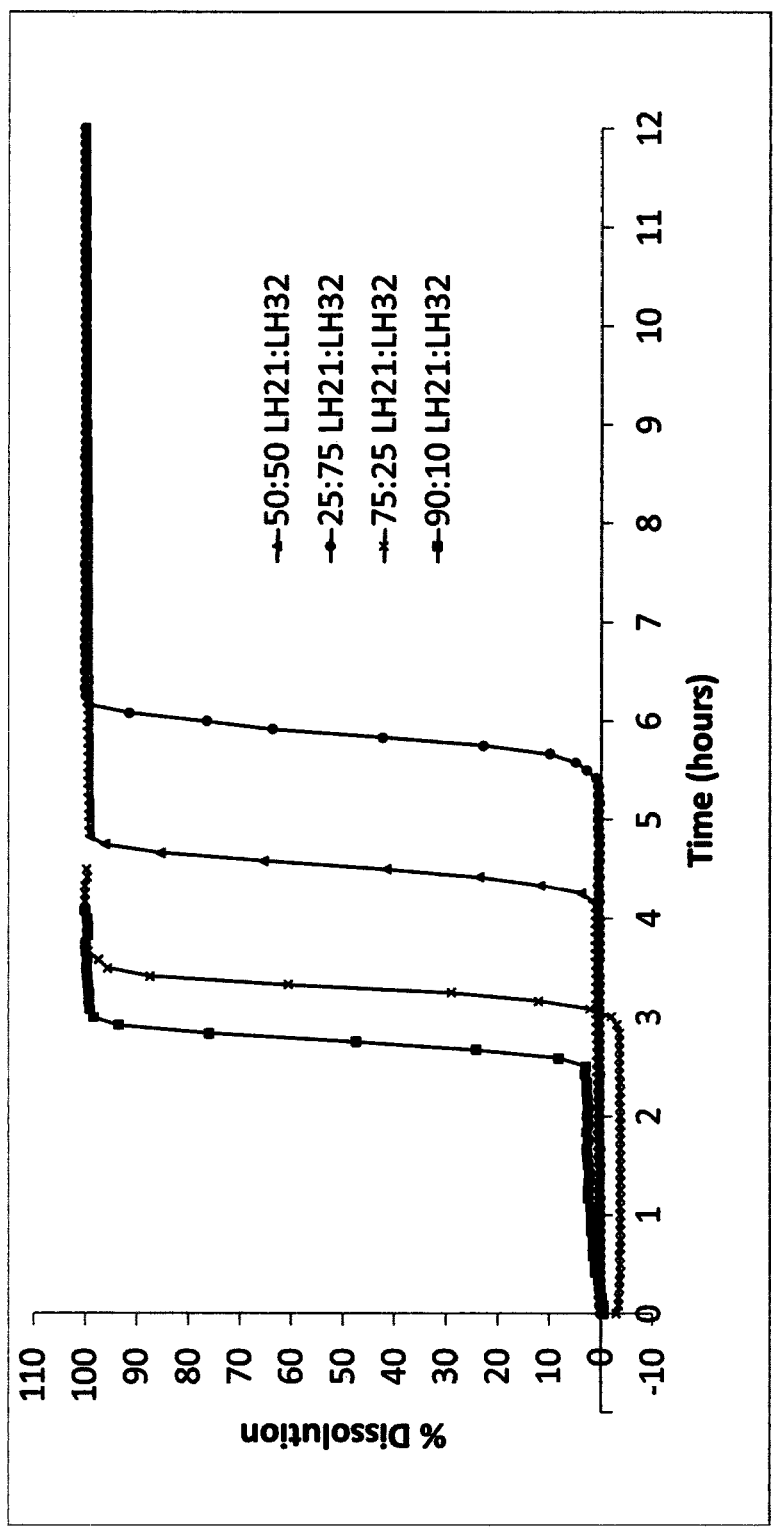
FIG. 4 shows dissolution profiles obtained for tablets according to the present invention wherein the wax content in the release barrier and overall weight of release barrier has been kept constant. The ratio of the L-HPCs used in this study (being LH-21 and LH-32) are however varied.

FIG. 4 shows the results of an examination of the release profile (according to 4. above) of diclofenac potassium from a composition according to the present invention and manufactured according to that described in numbered paragraphs 2 and 3 above, with proportions of wax and combinations of L-HPC as shown in table 6. The wax content in the release barrier and overall weight of release barrier has been kept constant. The ratio of the L-HPCs used in this study (being LH-21 and LH-32) are as follows: −25:75, 50:50, 75:25 and 90:10.

As we see from the graph below, increasing the amount of LH32 relative to LH21 results in an increase in the delay time. Previous studies found that LH32 when used on its own (i.e. in a formulation according to the present invention, but for the fact only a single grade of L-HPC is incorporated into the release barrier) provided a longer lag time than LH21 used on its own. A problem with this single L-HPC formulation was found, in that when used on its own, LH32 did not erode, instead the formulation opened up by a rupturing mechanism. Therefore manipulation of the LH ratios allows a more controlled release over longer lag times, while maintaining the key property of erosion.

TABLE 6

| Composition | 25:75 LH21:LH32 | 50:50 LH21:LH32 | 75:25 LH21:LH32 | 90:10 LH21:LH32 |
|---|---|---|---|---|
| Average release time (hh:mm) | 05:33 | 04:13 | 03:05 | 02:30 |
| Standard deviation | 00:07 | 00:02 | 00:05 | 00:05 |
| RSD (%) | 2.3 | 1.1 | 3.1 | 3.3 |

(RSD = relative standard deviation)

9. EFFECT OF DIFFERENT ACTIVE INGREDIENTS IN TABLET CORE

Figure 5:
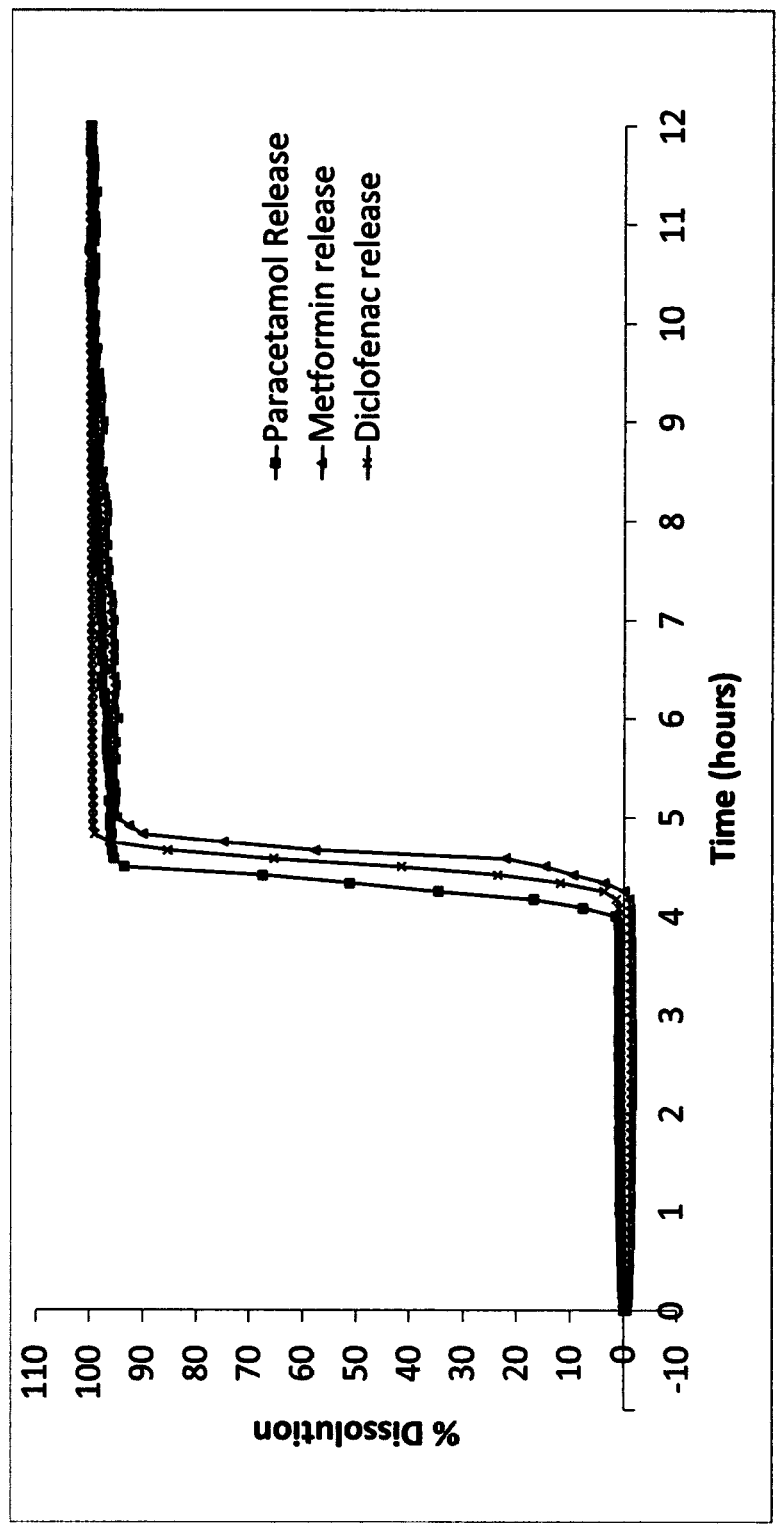
FIG. 5 shows dissolution profiles for tablets prepared according to the present invention and that include variations in the active ingredient to be released from the core.

FIG. 5 shows that the active ingredient in the tablet core has no effect of the lag period before release of active ingredient. The proportions of wax and combinations of L-HPC are kept constant for each tablet and are as shown in table 7. The tablets in the study however differ from each other by the choice of active ingredient provided in their core. Different active ingredients that are incorporated into the core of the studied tablets are selected from the following: Paracetamol 25 mg, Metformin 25 mg and Diclofenac 25 mg.

As can be seen from the results (after practicing analysis according to 4. above), the performance of the formulations of the present invention was not affected by the choice of active ingredient to be delivered by the formulations. Consequently, it can be concluded that the tablets of the present invention are a good vehicle for delivery of any active ingredient to be administered orally.

TABLE 7

| | Proportions described above of 42:22:36 relate to wax:LH21:LH32. | | |
|---|---|---|---|
| Composition | Paracetamol Core (42:22:36) | Metformin Core (42:22:36) | Diclofenac Core (42:22:36) |
| Average release time (hh:mm) | 04:11 | 04:23 | 04:13 |
| Standard deviation | 00:11 | 00:10 | 00:02 |
| RSD (%) | 4.38 | 3.8 | 0.8 |

10. EFFECT OF THICKNESS OF RELEASE BARRIER

Figure 6:
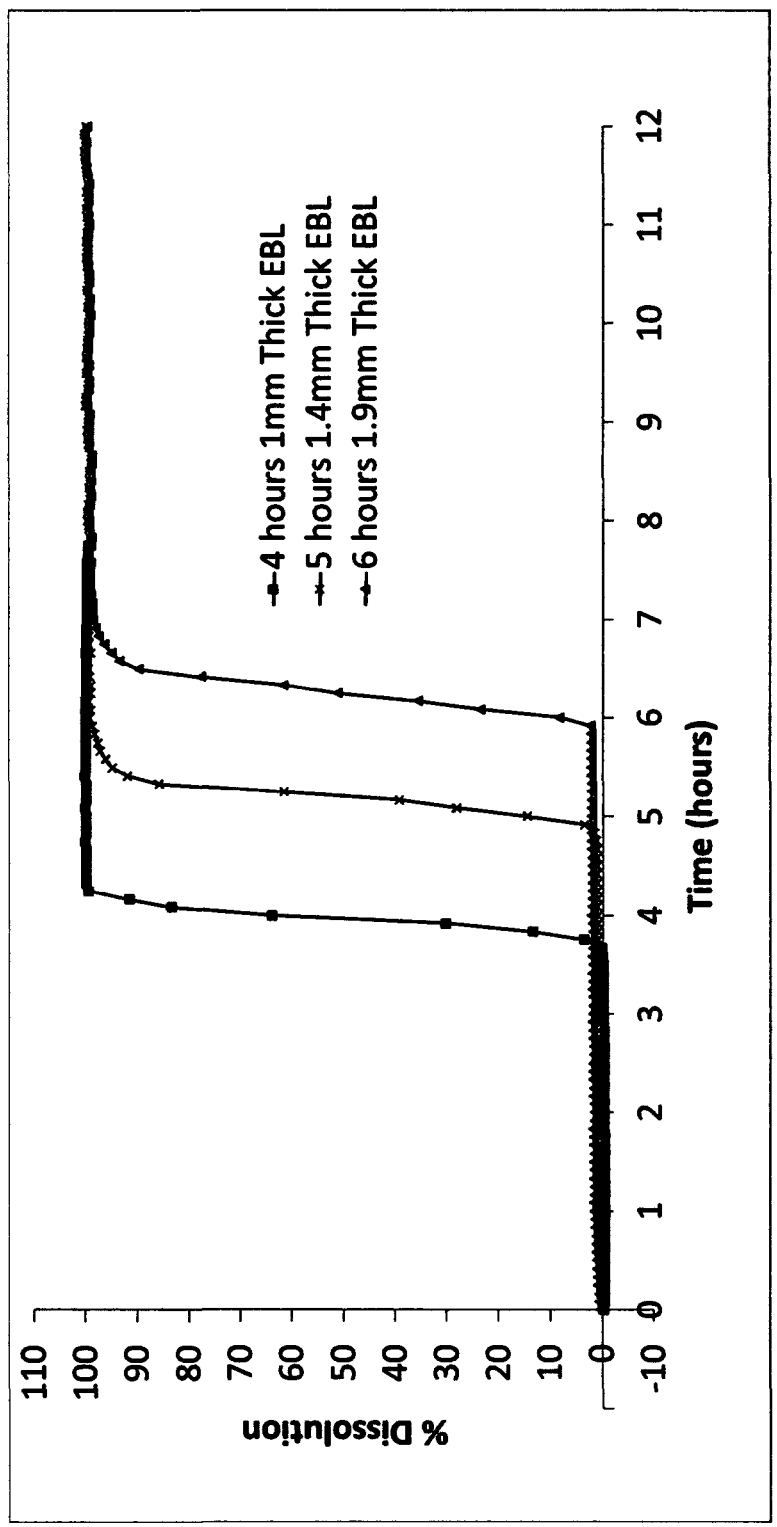
FIG. 6 shows dissolution profiles obtained for tablets according to the present invention and with varying release barrier thicknesses and a fixed formulation content in the release barrier.

FIG. 6 shows the results of an examination of the effect of thickness of release barrier on the release profile (as described in 4. above) of diclofenac potassium from a composition according to the present invention and manufactured according to that described in numbered paragraphs 2 and 3 above, with proportions as provided in table 8. The proportions of wax and combinations of L-HPC are kept constant for each tablet, i.e. 42:22:36 for GB:LH21:LH32.

As we see from the FIG. 6, increasing the amount of barrier layer we add to the core tablet results in an increase in the delay time before release. Thickness was measured using digital callipers on a tablet that has been broken in half to reveal the layers. The value for the thickness of the core was subtracted from the total thickness of the tablet in order to provide a value for the thickness of the release barrier.

TABLE 8

| Composition | 1 mm thick release barrier layer | 1.4 mm thick release barrier layer | 1.9 mm thick release barrier layer |
| --- | --- | --- | --- |
| Average release time (hh:mm) | 03:43 | 04:58 | 06:03 |
| Standard deviation | 00:02 | 00:11 | 00:10 |
| RSD (%) | 0.90 | 3.69 | 2.75 |

11. EFFECT OF COMBINATION OF L-HPC COMPARED TO SINGLE L-HPC IN A FORMULATION

Figure 7A:
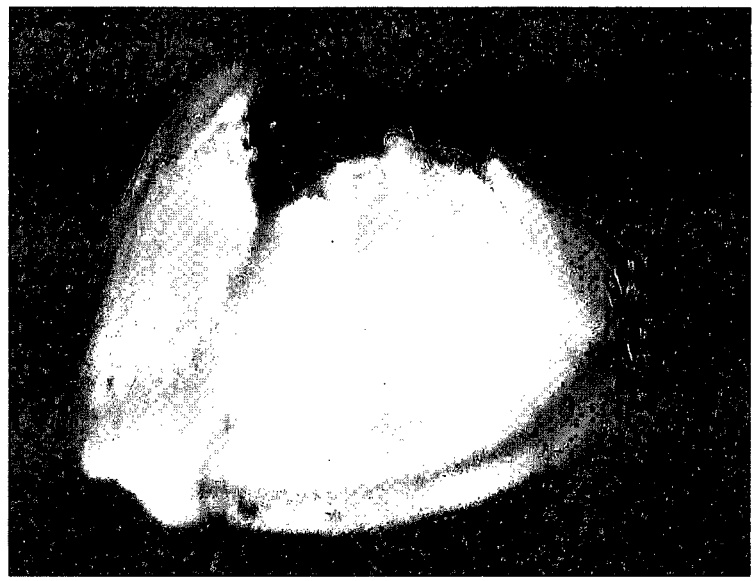
FIG. 7 shows an image of erosion of tablet made according to the present invention (B) compared to the rupture of a tablet that includes only a single grade of L-HPC (A).
Figure 7B:
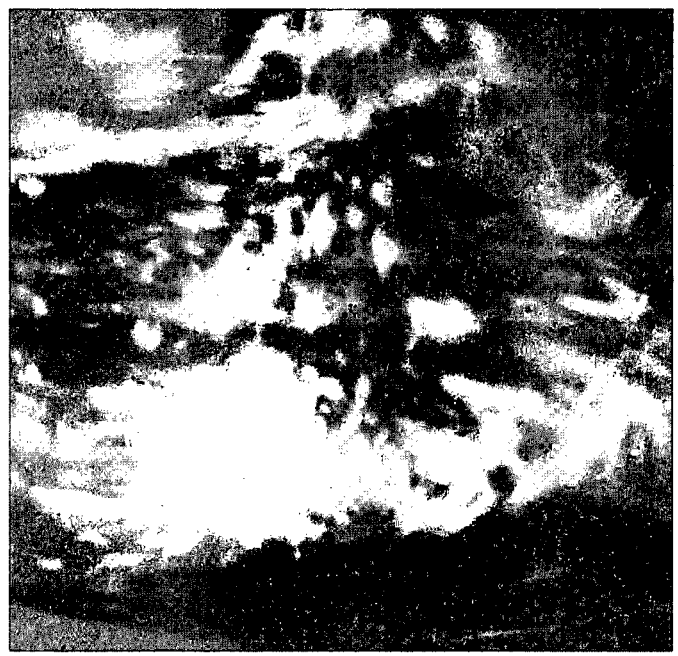

A first tablet was prepared according to the present invention and as described in 2. and 3. above. A second tablet was prepared, differing only by the fact that it contained 58% by weight of the release layer of LH-32 (i.e. as the only L-HPC in the formulation). The erosion of each tablet was studied according to that described in 4. above. Images taken at the point of release of active agent for each tablet is captured in FIG. 7(A), relating to the second tablet, and FIG. 7(B), relating to the first tablet.

It is clear from these images that the formulation including only a single L-HPC ruptured abruptly into a clam-shell, whereas the tablet formulated according to the present invention showed a more gradual erosion.

The invention claimed is:

1. A press coated tablet for delayed release of an active ingredient comprising:
   (a) a core comprising one or more active ingredients, and;
   (b) an erodible delayed release barrier surrounding the core and comprising a wax and two or more grades of low-substituted hydroxypropyl cellulose (L-HPC), wherein the wax and L-HPC are provided in a weight ratio of wax to L-HPC of from 30%:70% to 70%:30%.

2. The press coated tablet as claimed in claim 1, wherein the two or more grades of L-HPC include coarse and medium particle L-HPCs.

3. The press coated tablet as claimed in claim 2, wherein the two or more grades of L-HPC are selected from any one of the following combinations: LH-11 and LH-21, LH-11 and LH-22, LH-11 and NBD-22, LH-11 and NBD-021, LH-11 and NBD-020, LH-B1 and LH-21, LH-B1 and LH-22, LH-B1 and NBD-22, LH-B1 and NBD-021, LH-B1 and NBD-020.

4. The press coated tablet as claimed in claim 1, wherein the two or more grades of L-HPC include coarse and micronised particle L-HPCs.

5. The press coated tablet as claimed in claim 4, wherein the two or more grades of L-HPC are selected from any one of the following combinations: LH-11 and LH-31, LH-11 and LH-32, LH-B1 and LH-31, and LH-B1 and LH-32.

6. The press coated tablet as claimed in claim 1, wherein the two or more grades of L-HPC include medium and micronised particle L-HPCs.

7. The press coated tablet as claimed in claim 6, wherein the two or more grades of L-HPC are selected from any one of the following combinations: LH-21 and LH-31, LH-22 and LH-31, NBD-22 and LH-31, NBD-021 and LH-31, NBD-020 and LH-31, LH-21 and LH-32, LH-22 and LH-32, NBD-22 and LH-32, NBD-021 and LH-32, and NBD-020 and LH-32.

8. The press coated tablet as claimed in claim 1, wherein the two or more grades of L-HPC include a low and a high level hydroxypropoyl content L-HPCs.

9. The press coated tablet as claimed in claim 8, wherein the two or more grades of L-HPC are selected from any one of the following combinations: NBD-021 and NBD-022, NBD-020 and NBD-022, LH-11 and NBD-022, LH-21 and NBD-022, LH-31 and NBD-022, LH-B1 and NBD-022, NBD-021 and LH-22, NBD-020 and LH-22, LH-11 and LH-22, LH-21 and LH-22, LH-31 and LH-22, LH-B1 and LH-22, NBD-021 and LH-32, NBD-020 and LH-32, LH-11 and LH-32, LH-21 and LH-32, LH-31 and LH-32, and LH-B1 and LH-32.

10. The press coated tablet as claimed in claim 1, wherein the two or more grades of L-HPC include a low and a high level hydroxypropoyl content L-HPCs that are also a combination of coarse and medium particle L-HPCs.

11. The press coated tablet as claimed in claim 10, wherein the two or more grades of L-HPC are selected from any one of the following combinations: LH-11 and LH-22, LH11 and NBD-022, LH-B1 and LH-22, and LH-B1 and NBD-022.

12. The press coated tablet as claimed in claim 1, wherein the two or more grades of L-HPC include a low and a high level hydroxypropyl content L-HPCs that are also a combination of coarse and micronised particle L-HPC.

13. The press coated tablet as claimed in claim 12, wherein the two or more grades of L-HPC are selected from any one of the following combinations: LH-11 and LH-32, and LH-B1 and LH-32.

14. The press coated tablet as claimed in claim 1, wherein the two or more grades of L-HPC include a low and a high level hydroxypropyl content L-HPCs that are also a combination of medium and micronised particle L-HPC.

15. The press coated tablet as claimed in claim 14, wherein the two or more grades of L-HPC are selected from any one of the following combinations: LH-22 and LH-31, NBD-022 and LH-31, LH-21 and LH-32, NBD-021 and LH-32, and NBD-020 and LH 32.

16. The press coated tablet as claimed in claim 1, wherein the core tablet releases at least 70% of the active agent within 5-80 minutes after initiation of release.

17. The press coated tablet as claimed in claim 1, wherein the core tablet releases in a sustained manner over a period of 2-12 hours after initiation of drug active ingredient release.

18. The press coated tablet according to claim 1, wherein the wax is beeswax, microcrystalline wax, a glyceryl ester, hydrogenated castor oil, carnauba wax, or any combination of waxes.

19. The press coated tablet as claimed in claim 18, wherein the wax is glycerol behenate.

20. The press coated tablet according to claim 1, further comprising one or more coatings that can be pH dependent or independent or may be functional or aesthetic.

21. The press coated tablet according to claim 20 where the one or more coating contain an active ingredient that is the same as or different from the active ingredient or ingredients of the core.

22. The press coated tablet according to claim 1, further comprising a top layer which contain an optional immediate release layer comprising the same or different drug from that in the core.

23. A method of making the press coated tablet of claim 1, the method comprising the steps of:
   a) the active ingredient and pharmaceutically acceptable excipients and/or diluents are mixed or granulated together and compressed to form a core;
   b) one or more wax and two or more L-HPCs are mixed and melted to form granules and the resulting mixture compressed around the outer surface of the core so as to form a barrier layer.

24. The press coated tablet according to claim 1, wherein the erodible delayed release barrier lacks hydroxypropyl cellulose (HPC).

* * * * *